United States Patent
Ross

(10) Patent No.: US 6,391,330 B1
(45) Date of Patent: May 21, 2002

(54) PROANTHOCYANIDINS AND ASCORBIC ACID COMPOSITION FOR TOPICAL APPLICATION TO HUMAN RESPIRATORY AND ORAL MUCOSA

(76) Inventor: Michael A. Ross, 205-1900 Richmond Ave., Victoria, British Columbia (CA), V8R 4R2

( * ) Notice: Subject to any disclaimer, the term of this patent is extended or adjusted under 35 U.S.C. 154(b) by 0 days.

(21) Appl. No.: 09/569,273

(22) Filed: May 11, 2000

(51) Int. Cl.$^7$ .............................................. A61F 13/00
(52) U.S. Cl. ....................................... 424/434; 424/45
(58) Field of Search ..................... 424/434, 54, 78.3, 424/45; 514/474

(56) References Cited

U.S. PATENT DOCUMENTS

| | | | |
|---|---|---|---|
| 5,470,874 A | 11/1995 | Lerner | 514/474 |
| 5,494,661 A | 2/1996 | Tempesta | 424/78.38 |
| 5,844,061 A | 12/1998 | Vercauteren et al. | 528/86 |
| 5,906,811 A | 5/1999 | Hersh | 424/54 |
| 6,180,663 B1 * | 1/2001 | Lang | 514/44 |

OTHER PUBLICATIONS

"Indoor Air Quality Recommendations Relevant to Aircraft Passenger Cabins" Hocking et al American Industrial Hygiene Association Journal Jul. 1998; pp. 446–454.

* cited by examiner

Primary Examiner—Thurman K. Page
Assistant Examiner—Robert M. Joynes
(74) Attorney, Agent, or Firm—Hayes Soloway P.C.

(57) ABSTRACT

A nasal and pharyngeal spray solution for use in spraying into the nose and mouth to protect the mucosa from noxious viruses, bacteria and fungi and excessive drying, in situations of high risk, such as the cabins of commercial aircraft, is comprised of a saline solution of Proanthocyanidins and ascorbic acid. The 'fresh mix' delivery system is an appropriately closed, sterile, oxygen-excluding, pressurized container.

3 Claims, No Drawings

PROANTHOCYANIDINS AND ASCORBIC ACID COMPOSITION FOR TOPICAL APPLICATION TO HUMAN RESPIRATORY AND ORAL MUCOSA

The present invention relates in general to nasal and pharyngeal spray composition and, more specifically, to a nasal and pharyngeal sprays particularly suited for use by aircraft passengers.

BACKGROUND OF THE INVENTION

There is a growing concern among the travelling public that the cabins of commercial aircraft are a breeding space for infection. As indicated by Hocking M. B., in American Industrial Hygiene Journal 59: 446–454 1998, "Aircraft passengers, particularly on international flights, represent some of the most diverse assemblies of people placed into a closely packed situation for long periods with the smallest provision of fresh air of any group requirement of our society today". Viral and bacterial contamination from a maximally compressed arrangement of individuals in varying states of health, sharing partially recycled air, in a confined space increases the opportunity for the spread of disease. Up to 52% of air in commercial aircraft supplied to passengers may be re-circulated. On a fully loaded plane, passengers may have one-tenth of the available airspace of a full theatre. The low humidity of cabin air, as low as 15%, impairs the self cleansing qualities of the nose. Proximity of the passenger seating arrangements increase the risk of the spread of droplet dispersion.

The nose is normally protected from infection by the constant flow of mucus from anterior to posterior. This is achieved by the cilia (small hair-like projections of the cells of the respiratory mucosa) wafting the mucus posteriorly with a normal transit time of 11 minutes. Under conditions of very low humidity, the mucus blanket may dry and become too viscous to move normally or even dry out and crack, allowing inhaled viruses to make direct contact with respiratory cells causing infections.

The humidity of commercial aircraft cabins may reach levels as low as 15%, and in long flights this represents a serious challenge to normal nasal function. Humidifying the air in the whole cabin of the aircraft is currently not practical and might result in fungal contamination of the entire ventilating system.

The synergy of combining Proanthocyanidins with ascorbic acid is known. Lerner U.S. Pat. No. 5,470,874, granted on Nov. 28, 1995 for "Ascorbic Acid and Proanthocyanidine Composition for Topical Application to Human Skin", discloses a composition which includes the two substances, restricted to use on the skin only and includes methylparaben, Xanthum gum and preservatives. Hersh U.S. Pat. No. 5,906,811, granted on May 25, 1999 for "Intra-oral Antioxidant Preparations", proposes a large array of alternative ingredients, some in concentrations irritating to the respiratory mucosa, without targeting the specific benefits of Proanthocyanidins and ascorbic acid. The proposed product is a mouthwash. In general, the topical use of Proanthocyanidins (Pycnogenol™) on nasal mucosa has not been investigated.

Clearly, there is a need for solution for use by passengers to overcome these difficulties.

My own investigations of these two agents in combination have attested to their tolerance in the nose and throat at the specified concentrations and their anti-viral, anti-fungal effectiveness. Furthermore, personal investigations have shown that Proanthocyanidins will eliminate the yeast Candida from the upper air and food passages.

SUMMARY OF THE INVENTION

The present invention seeks to provide a mechanism which allows individual passengers to maintain a more normal nasal performance and to reduce the risk of ambient viruses. Broadly stated, the present invention is defined as a nasal and pharyngeal spray composition comprising a saline solution of Proanthocyanidins and ascorbic acid.

The present invention exhibits anti-viral, anti-bacterial and anti-fungal capabilities designed to help prevent and be an early treatment for upper respiratory infections in situations where contaminated, recycled air, low humidity, and congestion, such as in commercial aircraft cabins, which present a high risk environment. If used by passengers who already have an upper respiratory infection, it would likely reduce the risk of spreading contamination. The anti-oxidant Proanthocyanidins are used as anti-viral and anti-bacterial agents enhanced by the combination with ascorbic acid.

DETAILED DESCRIPTION OF THE PREFERRED EMBODIMENT

The present invention is generally defined as a nasal and pharyngeal spray composition comprising a saline solution of Proanthocyanidins and ascorbic acid. The Proanthocyanidins may be in the range of 250–750 mg. per 100 mL solution. The ascorbic acid may be in the range of 50–150 mg per 100 mL solution. The saline solution may be 700 mg sodium chloride (NaCl) per 100 mL water, weight/volume. Preferably, the composition comprises 500 mg. Proanthocyanidins/100 mL solution; 50 mg. ascorbic acid/100 mL solution; and 100 mL 0.7% Saline.

The comfort tolerance of any stimulus to the nasal mucosa is extremely variable. Most individuals tested are comfortable with this range of concentrations. Combining the two active substances has reduced the need for higher concentrations of each to acceptable comfort levels by the mechanism of synergy.

The solution will be sterile and no preservatives will be added which could have unpredictable effects on the Proanthocyanidins. Simple buffering agents such as sodium hydroxide may be added to maintain a pH of 5.5 to 6.5. In the design experiments for the invention, the source of proanthocyanidin was the bark of the "*Pinus maritinus*" (Pycnogenol™) through the courtesy of Horphag Research. Other sources of Proanthocyanidins, such as grape seeds could be used but would not have the same consistent or controlled composition.

There are three primary reasons for adding ascorbic acid to Proanthocyanidins in the solution. Ascorbic acid prolongs the duration of the effectiveness of Proanthocyanidins in the container. It has a synergistic action with Proanthocyanidins so that the two combined are more effective than either alone. Ascorbic Acid catalyses the immune response to infections and it has a powerful effect on the scavenging of free radicals.

The container for the solution of Proanthocyanidins and ascorbic must meet several exacting criteria to be effective. Certain existing containers can be readily modified to meet the following five requirements. First, it must be a closed system excluding oxygen which would destroy the anti-oxidant effect. Second, the closed system must exclude bacteria as the use of any preservative may have unpredictable and undesirable results. Third, the container must allow for closed and sterile mixing of the two substances immediately before use. Fourth, the solution must be consistently pressurized to discourage the entry of any foreign matter or bacteria and the pressure must be comfortable for the sensitive nasal tissues. The configuration of the spray nozzle must create a fine mist within the nasal cavities. Fifth, the active substances must be maintained in a dry form within the container until ready for use. When the spray nozzle is inserted into the container it will break a seal allowing the two very soluble substances to mix with the saline. The effective life of the "fresh mix" solution is one month if refrigerated.

The anti-viral effectiveness of Proanthocyanidins has been described in the skin and in the eye when topically applied. Nasal inhalation, however, for the purpose of preventing infection, has not been described in available literature. Personal investigations have shown that Proanthocyanidins will eliminate the yeast Candida from the upper air and food passages.

Proanthocyanidins studies have shown in vitro, anti-viral activity frequently approaching that of ribavarin in tests with respiratory syncytial viruses, para influenza and influenza A & B. For proplylaxis, before the virus has gained cellular entry, the effectiveness should be even more satisfactory.

Furthermore, the anti-oxidant Proanthocyanidins have an effect on the surface of the mucosa, protecting it from noxious substances including ozone, which has a greater than normal concentration in aircraft cabins during flights. They have a stabilizing influence on capillary permeability and leakage reducing the negative influence of altitude.

Proanthocyanidins are absorbed through the nasal mucosa. This ensures that its protective influence in the nose is much more prolonged than the eleven minutes of surface contact. The transit time that it takes for non-absorbed substances to travel from the anterior nose to the pharynx.

I claim:

1. A nasal and pharyngeal spray composition comprising a saline solution of Proanthocyanidins and Ascorbic acid, wherein said composition includes between 250–750 mg. Proanthocyanidins per 100 mL solution and between 50–150 mg. Ascorbic acid per 100 mL solution, and said saline solution includes 700 mg. NaCl/100 mL $H_2O$, weight/volume.

2. A nasal and pharyngeal spray composition comprising:
   500 mg. Proanthocyanidins per 100 mL solution;
   50 mg. Ascorbic acid per 100 mL solution; and
   100 mL 0.7% saline.

3. A nasal and pharyngeal spray composition as defined in claim 2, said saline including 700 mg. NaCl/100 mL $H_2O$, weight/volume.

* * * * *